United States Patent [19]

Marsh et al.

[11] 4,076,800
[45] * Feb. 28, 1978

[54] PROTEIN-CONTAINING DETERGENT COMPOSITIONS FOR PROTECTING KERATINOUS MATERIALS

[75] Inventors: Robert Anthony Marsh, Newcastle-upon-Tyne, England; Gordon John Mackie, Strombeek-Bever; Peter Hale, Tervueren, both of Belgium

[73] Assignee: The Procter & Gamble Company, Cincinnati, Ohio

[*] Notice: The portion of the term of this patent subsequent to Sep. 14, 1993, has been disclaimed.

[21] Appl. No.: 647,245

[22] Filed: Jan. 7, 1976

[30] Foreign Application Priority Data

Jan. 13, 1975 United Kingdom ............... 1319/75

[51] Int. Cl.$^2$ ....................... A61K 7/06; A61K 7/48
[52] U.S. Cl. ........................... 424/70; 252/DIG. 2; 252/DIG. 3; 252/DIG. 13; 252/142; 252/545; 252/550; 252/551; 252/554; 252/558; 424/DIG. 2; 424/359
[58] Field of Search .............. 424/DIG. 2, 70, 359; 252/DIG. 2, DIG. 3, DIG. 13, 545, 550, 142, 551, 554, 558

[56] References Cited

U.S. PATENT DOCUMENTS

| 1,965,008 | 7/1934 | Sponsel et al. | 260/117 |
|---|---|---|---|
| 2,113,819 | 4/1938 | Tucker | 260/112 R |
| 2,282,001 | 5/1942 | Russell et al. | 260/117 |
| 2,363,892 | 11/1944 | Monier | 260/117 |
| 3,340,153 | 9/1967 | Kast | 424/359 |
| 3,548,056 | 12/1970 | Eigen et al. | 424/171 |
| 3,642,977 | 2/1972 | Hewitt | 424/70 |
| 3,738,913 | 6/1973 | Johnsen et al. | 424/359 X |
| 3,787,337 | 1/1974 | Goodwin | 252/545 |
| 3,824,228 | 7/1974 | Eckert et al. | 260/117 |
| 3,898,129 | 8/1975 | Fujimoto et al. | 252/544 X |
| 3,898,186 | 8/1975 | Mermelstein et al. | 252/546 X |
| 3,904,748 | 9/1975 | Eckert et al. | 424/70 |
| 3,907,580 | 9/1975 | van Ham | 424/359 X |
| 3,954,725 | 5/1976 | Johnsen et al. | 260/112 R |

FOREIGN PATENT DOCUMENTS

| 278,250 | 1/1970 | Austria | 424/70 |
|---|---|---|---|
| 877,909 | 8/1971 | Canada | 424/359 |
| 120,311 | 5/1971 | Denmark | 260/123.5 |
| 1,157,928 | 6/1958 | France | 424/70 |
| 2,053,195 | 4/1971 | France | 424/70 |
| 722,596 | 7/1942 | Germany | 424/359 |
| 1,192,370 | 5/1965 | Germany | 424/71 |
| 2,151,740 | 4/1973 | Germany | 424/70 |
| 1,057,418 | 2/1967 | United Kingdom | 424/70 |
| 1,122,076 | 7/1968 | United Kingdom | 424/47 |
| 1,224,798 | 3/1971 | United Kingdom | 424/70 |
| 1,254,309 | 11/1971 | United Kingdom | 424/70 |
| 1,276,960 | 6/1972 | United Kingdom | 424/70 |

OTHER PUBLICATIONS

Schimmel Briefs, No. 348, Schimmel & Co., Newburgh, Jan. 1965.

Primary Examiner—Albert T. Meyers
Assistant Examiner—Vera C. Clarke

[57] ABSTRACT

Detergent Compositions having a protective effect on keratinous material incorporate a proteinaceous material whose primary amino or carboxylic acid side chain groups have been modified by reaction with $C_1$–$C_7$ acyl- or alkyl- group-containing materials respectively to give a modified protein of isoionic point (pI) less than pH 6. Granular, bar and liquid detergent formulations embodying the invention are disclosed.

8 Claims, No Drawings

PROTEIN-CONTAINING DETERGENT COMPOSITIONS FOR PROTECTING KERATINOUS MATERIALS

FIELD OF THE INVENTION

This invention relates to compositions which protect keratinous material, such as skin or hair, from the deleterious effects of detergents or other harsh materials such as solvents, and from adverse climatic conditions.

The compositions of the invention accordingly help to maintain the keratinous material in good condition. The invention also relates to a method of treating keratin.

BACKGROUND OF THE INVENTION

The deleterious effects of compositions containing surfactants upon keratin are well known. These effects are caused, it is thought, by penetration of the surfactant into the keratin surface leading to "leaching out" of oils and moisturizing components essential for good condition of the keratin. This penetration by surfactant and "leaching out" of essential oils also affects the ability of the keratin, particularly in the case of skin, to retain water within the tissue and this again leads to poor condition of the keratinous material.

Many attempts have been made in the past to provide compositions for maintaining or improving the condition of skin and hair. The application of protein to skin and hair as cosmetic treatments probably antedates recorded history. Casein, in the form of milk, has been used as a time-honoured beautifier and more recently has been recommended for use in toilet soaps. U.K. Pat. No. 1,160,485 describes the inclusion of partially degraded water soluble proteins having a gel strength of zero Bloom grams in detergent compositions and lotions for application to skin as dishwashing liquids.

German Offenlegungsschriften (Published Specifications) Nos. 2,151,739 and 2,151,740 describe certain fatty derivatives of low-molecular-weight aminolysates suitable for use in shampoos. U.K. Pat. No. 1,122,076 describes the preparation of low-molecular-weight, alcohol-soluble protein esters suitable for use in hair-spray formulations. Various low-molecular-weight polypeptides or modified polypeptides are commercially available and recommended for use in cosmetic and shampoo formulations, for instance Hydro Pro 220, and Hydro Pro 330 marketed by the Stepan Chemical Company; and Wilson X250, Wilson X1000 and Wilson Aqua Pro marketed by the Wilson Chemical Company. However, it has been found that none of these compositions are especially effective in protecting keratin from the action of harsh detergents, and this is particularly true when the proteins are incorporated in the detergent composition itself. The emolliency of these compositions can often be improved by addition of fatty or oily materials but, when used in dishwashing liquids, this usually leads to loss of foaming power or aesthetic changes which are generally considered undesirable by consumers.

SUMMARY OF THE INVENTION

The present invention therefore provides protein-containing compositions which are particularly effective in protecting keratinous material, such as skin or hair, from the deleterious effects of detergents and other harsh materials and from adverse climatic conditions, which compositions are effective even when applied to keratin in foaming detergent solutions and which result in no loss of foaming or cleaning power for detergent solutions containing them.

Accordingly, the present invention provides a composition for protecting keratinous material from the deleterious effects of detergent and other harsh materials and from adverse climatic conditions, the composition comprising a foaming, non-cationic detergent material and a chemically modified protein (as hereinafter defined) having an isoionic point less than pH6 in which at least a portion of the precursor protein carboxylic acid groups or primary amino groups replaced by —(CO)Q and —NHYQ respectively, where Y is a direct link, carbonyl or sulfonyl groups and Q represents R, SR, OR or NHR, with R comprising alkyl, alkenyl, aryl, cycloalkyl or heterocyclyl moieties and containing no more than seven carbon atoms, the alkyl or alkenyl moieties optionally being interrupted by heteroatoms or substituted with nonionic or cationic radicals.

DETAILED DESCRIPTION OF THE INVENTION

In this specification a modified protein means a product, other than a derived protein, obtained in one or more stages by chemical modification of a precursor protein, a precursor protein being a non-enzymic protein chosen from natural, derived, synthetic or biosynthetic proteins, and a derived protein being the product of hydrolytic, ammoniolytic, enzymic or thermal degradation of a protein material. Precursor protein also covers low molecular weight materials which may, more strictly, be termed polypeptides and peptides.

According to a further aspect of the invention, there is provided a method of protecting keratinous material from the deleterious effects of detergent and other harsh materials, the method comprising treating keratin with an aqueous solution or dispersion of the composition of the invention.

The precursor proteins suitable for use, after modification, in the compositions of the invention, may be chosen from natural, derived, synthetic or biosynthetic proteins. Natural proteins may be of either animal or vegetable origin and include simple and conjugated protein.

Typical natural proteins include intracellular proteins and globular proteins such as those present in blood plasma and milk, as well as solubilized collagen and protein isolates from nuts, cereals etc. such as soybean isolate, peanut protein, cotton seed protein etc. Derived proteins may be obtained from many sources, for instance by hydrolytic, ammoniolytic, thermal or enzyme degradation of globular or structural proteins such as keratin, collagen, fibrinogen, myosin, whey, egg white, casein or vegetable proteins such as those obtained from cereals, nuts, soybean curd or the protein-rich residues from seed-oil manufacture. Preferred synthetic proteins include polylysine and unicellular proteins obtained from bacterial micro-organisms.

Protein primary amino group modification takes place primarily at lysine groups and, desirably, the precursor protein should have at least 4 gms., preferably at least 6 gms. of lysine per 100 gms. of protein. Suitable precursor proteins in this class include the milk proteins, casein and whey, and egg white proteins (primarily ovalbumin), bacterially derived unicellular protein and soy, or derived proteins prepared therefrom. In addition, suitable precursor proteins should comprise at least 20 gms. of aspartyl and glutamyl groups, in total, per 100 gms. of protein. Amino acid contents for a wide variety of proteins are given on page 105 of Amino Acids and Proteins by D. M. Greenberg published by Charles Thomas in 1951, which disclosure is hereby incorporated by reference.

Of the above-detailed modified proteins, preferred are those proteins in which R has the formula:

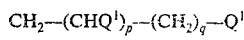

in which $Q^1$ is $R^1$, $-SR^1$, $-OR^1$, or $NHR^1$ in which $R^1$ is a hydrogen atom or an alkyl or alkenyl moiety, $p$ is 0 or 1 and $q$ is from 0 to $(5-p)$.

Preferred classes of modified protein falling within the above definitions are those in which R is represented by:

(1) $CH_2-CH(OH)-(CH_2)_r-H$ in which $r$ is from 0 to 4, and
(2) $CH_2-(CH_2)_r-H$ in which $r$ is from 0 to 3.

The modified proteins of the present invention are made by modification of protein precursor side chains comprising free carboxylic acid groups or free primary amino groups. In particular, modification of acid groups preferably takes the form of oxyalkylation and esterification or amidation. Modification of the basic groups, on the other hand, preferably takes the form of acylation and alkylation.

Methods of preparation of proteins having these functional substituents are well known in the art and the necessary preparative techniques are described in "The Chemical Modification of Proteins" by G. E. Means and R. E. Feaney published by Holden-Day Inc. in 1971, the disclosures of which are hereby incorporated by reference. Although the principal reactive centers are the protein side-chains comprising carboxylic acid or primary amino groups, simultaneous modification of other reactive centres such as sulphydryl, aliphatic or phenolic hydroxy, imidazole or guanidino groups, may also occur. An exemplary modified protein has, as substituents, hydroxyalkyl ester groups derived from the carboxylic acid groups of the unmodified substrate and prepared by reaction of the protein with an epoxide, for example but-1-ene oxide.

In preferred embodiments of the invention, the proteins may be acylated or alkylated via primary amino groups. Acylation may be performed by using the appropriate acid anhydride or N-carboxy anhydride. In the latter case, this results in acylation predominantly at amino groups. In the former case, if the acid anhydride is cyclic, the modification leads to acidic substituents which should be neutralized, for instance by esterification. Reactions analogous to acylation may also be performed. Thus, primary amino groups may be converted to unsymmetrical disubstituted ureas by treatment with isocyanates. In addition, sulfonamide derivatives of proteins may be prepared, for instance, by reaction of protein primary amino groups with sulfonyl halides.

As stated above, exemplary modified proteins to be used in the present invention include hydroxyalkylation products of acid or base hydrolyzed or ammonolyzed soyprotein isolates, with molecular weights in the region from 1,000 to 10,000. Such modified proteins have proportionately fewer carboxylic acid groups and more carboxylic ester groups than the unmodified proteins. Lower alkyl or hydroxyalkyl ester derivatives are preferred. They may be prepared simply by treatment with an alkylene oxide, in which case esterification may be accompanied by hydroxyalkylation of other reactive species, for example primary amino groups. The extent of such N-hydroxyalkylation depends primarily on the pH conditions employed. If the pH of the reaction medium is held in the acid region during the course of the reaction, then the degree of N-hydroxyalkylation is rather less than if the pH is allowed to rise during the reaction.

Where it is intended to modify the carboxyl groups of the proteins, reaction conditions are adjusted so that at least 5%, preferably at least 20% and desirably at least 35% of the free carboxylic acid groups are modified. Modification of more than about 50% of the free carboxyl groups is difficult and also undesirable for the purposes of the present invention.

Particularly highly preferred proteins are the N-acyl and N-sulfonyl derivatives of degraded proteins, particularly of degraded casein, soyprotein and collagen (gelatin). The acyl group may be introduced by allowing an aqueous solution of the protein to stand at a temperature of 10°–20° C for 1–2 hours with the anhydride of the appropriate carboxylic acids, in particular acetic, propionic, n- and iso- butyric acids. The reaction may be conducted at a pH of from 6 to 9, especially from 7 to 8, using a suitable buffer to promote acylation rather than hydrolysis of the anhydride which occurs as a side-reaction.

The degree of acylation of the protein will depend upon the relative amounts of protein and anhydride used. Generally at least 20% of the protein primary amino groups will be acylated, preferably at least 40% and especially at least 60%; 80% or more acylation is readily achievable using a large (20 to 30 fold) excess of anhydride.

Condensation products with sulfonic acid derivatives are generally prepared via the corresponding sulfonyl chloride compounds. The sulfonyl chloride compound is conveniently obtained from the corresponding sulfonic acid by treatment with phosphorus pentachloride and is treated with an alkaline solution or dispersion of the protein at 50°–100° C for, e.g. 4–5 hours, with constant addition of aqueous alkali to maintain an alkaline pH.

Particularly preferred proteins for use in the compositions of the invention have characteristic values of molecular weight and isoionic-point pH and these will now be discussed in some detail.

It will be appreciated that the molecules of a protein vary widely in their size and complexity and that the molecular weight of a protein is necessarily an imprecise quantity. The molecular weight of a protein may be specified by defining the molecular weight distribution of the molecules of the protein, but it is usual to define, instead, the average molecular weight of the protein sample because it is an average molecular weight which is measured by most physical techniques. Such an average is only an approximate guide, however, to the actual molecular weight distribution of the sample. Also, it should be appreciated that the average molecular weight as measured may vary from one measuring technique to another although the differences between the results of the various techniques generally diminish towards lower molecular weights. In this specification, one method employed for determining average molecular weights of proteins (for molecular weights greater than about 5000) makes use of viscometric measurements of buffered protein solutions. The intrinsic viscosity of a buffered protein solution is known to be primarily dependent upon the overall length of the protein coil and to be relatively independent of the nature of the sidechain and end groups of the protein. There is, therefore, a relationship between instrinsic viscosity and the average molecular weight of the protein, which may be expressed as $$[h] = K \cdot M^a \text{ [Staudinger's Equation]}$$

where $K$ and $a$ are constants for a particular source of protein. It is thus straightforward to determine molecular weights from viscosity measurements, knowing K and $a$, and this is fully described in Macromolecular Chemistry of Gelatin, page 72, by A. Veiss, and in Biochimica et Bisphysica Acta, 57, 222–9 (1961) by J. Bello, H. R. Bello, and J. R. Vinograd.

However, the viscosity method is not very accurate at molecular weights of about 5000 and below and ultracentrifuge techniques reveal only small differences in observed values for molecular weights up to about 80,000.

When measured by the above methods, the precursor and modified proteins of the present invention generally have molecular weights in the range from 300 to 50,000, preferably from 600 to 20,000, desirably from 1,000 to 10,000 and more especially from 2,000 to 5,000.

The modified proteins may be present in the compositions of the invention in an amount from 0.1 up to 20%, but generally in an amount between 1 and 10%, preferably between 2 and 6%, by weight of the composition.

Protein molecules, having both acidic and basic side chains, are charged in both acidic and basic solutions and thus are amphoteric in nature. The pH at which equal concentrations of protein anions and cations exist in solution is known as the isoionic point, and in the present invention, the isoionic point of the modified proteins must be less than 6, generally in the range 2.5 to 5.5, and preferably in the range 2.5 to 4.0. The isoionic point pH may be determined in the following manner:

Amberlite acid resin (IR 120) and base resin (IR 400) are washed with several volumes of water, filtered and mixed in the ratio 0.4:1. A solution (20 mls.) of protein (3%) and urea (20% by weight) is prepared with minimum warming and allowed to cool to constant temperature. The resin mixture (8.4g.) is added, the solution is stirred for 5 minutes, the mixture is filtered and the pH of the filtrate is the isoionic point pH of the protein.

Specific preparative methods for modified proteins useful in the present invention are as follows:

Oxyalkylation of Proteins

The following procedure is typical of methods which may be used for oxyalkylation of proteins. In this instance, the method is described with reference to the oxybutylation of alkali-degraded soyprotein.

Promine F (50g), an edible grade soybean isolate (Promine F being a Trade Mark) was added to vigorously stirred warm water (150 mls.) to form a slurry. The mixture was heated to a slurry temperature of 90°–95° C. and sodium hydroxide pellets (5g) were added. After stirring for 4 hours, the liquid was cooled to 30° C. and treated with hydrogen peroxide solution (2 mls. of 30%). The solution was stirred for 20 minutes at room temperature and the pH of the solution was adjusted to 5–6. The hydrolysis solution was then diluted with water (150 mls.), but-l-ene oxide (50 mls.) was added and the solution was stirred at 40°–60° C. for a period of 24–31 hours. After cooling, excess epoxide was distilled off, the solution was neutralized and the product isolated by freeze drying.

Variations of the above method may, of course, be employed. Thus the soyprotein may be degraded using a medium strength, 1:5 ammonia/water solution, or may be degraded by acid hydrolysis or by reductive cleavage with, for example, sodium borohydride. Other types of modified proteins may be used in place of soy derived protein, for example casein, gliadin, zein and serum or egg albumins. Other processes may be employed to obtain oxyalkylated derivatives, for example, reaction with anhydrous alkylene carbonates.

Acyl derivatives of proteins

Promine F (120g) was first hydrolyzed in water (360 mls.) containing sodium hydroxide (12g) as described earlier. After cooling, acetic anhydride (60 mls.) was added slowly to the solution over a period of about 1 hour, keeping the pH of the solution at about 7 to 8, by the addition of further sodium hydroxide, and maintaining the temperature below 20°. The solution was then stirred for a further hour, and the protein was precipitated by acidifying to pH 3 and cooling. The precipitate was washed with cold acid and the protein obtained by freeze drying. It had an isoionic point pH of about 3, a molecular weight of about 3000 and contained substantially no unacetylated $\epsilon$-amino groups.

A similar procedure was used to obtain higher acyl derivatives, although somewhat longer reaction times were required in these cases. The procedure was also applicable to the acylation of whole protein, such as whole casein, whey, serum albumin etc.

The optimum choice of protein for any particular composition depends to a certain extent upon the pH of the composition in use, i.e. the pH of the carrier upon application to keratin. This in-use pH may, depending upon the type of application, be the pH of the composition itself, or be the pH of an aqueous solution or dispersion of the composition at a concentration of use which may be as little as 0.01%.

In order to obtain the maximum occlusive benefit, compositions of the invention should have an in-use pH as different as possible from the pI of the modified protein. For modified proteins having a pI<6, the in-use pH is preferably greater than pH6 and desirably is greater than (pI + 2).

The in-use pH of the compositions of the invention may vary widely, of course, depending upon the purpose and manner of use of the compositions. Liquid compositions designed for shampoos are generally applied to hair in medium/high concentration aqueous solution, and the in-use pH is close to the pH of the composition itself. This may be any pH in the range, generally, from 4 to 9. Detergent compositions such as liquid dishwashing compositions, bathing compositions and heavy-duty granular or liquid detergents are usually used in a large excess of water, and the in-use pH is the pH of an aqueous solution of the composition at a concentration generally in the range from 0.01 to 2% by weight. Builder-free detergent compositions used, for instance, as light-duty detergents generally have an in-use pH of about 7; built heavy-duty detergents generally have an in-use pH in the alkaline range up to a pH of about 11. Soap bar compositions are applied to skin as an aqueous solution or dispersion of the soap bar ingredients at a concentration, generally in the range from 5 to 15 wt%. The pH of the soap dispersion may vary, depending upon the type of soap bar employed, from a pH of 5.5 to about 10.5

Surfactant materials which may be used in the compositions of the invention can be selected from foaming water-soluble soap and synthetic anionic, nonionic, zwitterionic and amphoteric detergents described as below. Cationic materials may be present but preferably only in the presence of other types of detergent.

A. Anionic Soap and Non-Soap Synthetic Detergents

This class of detergents includes ordinary alkali soaps such as the sodium, potassium, ammonium, alkyl ammonium and alkylolammonium salts of higher fatty acids containing from 8 to 24 carbon atoms and preferably from 10 to 20 carbon atoms. Suitable fatty acids can be obtained from natural sources, such as plant or animal esters (e.g. palm oil, coconut oil, babassu oil, soybean oil, castor oil, tallow, whale and fish oils, grease, lard, and mixtures thereof). The fatty acids also can be synthetically prepared (e.g. by the oxidation of petroleum or by hydrogenation of carbon monoxide by the Fischer Tropsch process). Resin acids are suitable, such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium, potassium, and triethanol-ammonium salts of the mixtures of fatty acids derived from coconut oil and tallow, e.g. sodium or potassium tallow and coconut soaps.

This class of detergents also includes water-soluble salts, particularly the alkali metal salts, of organic sulfuric reaction products having in their molecular structure an alkyl radical containing from 8 to 22 carbon atoms and a sulfonic acid or sulfuric acid ester radical. (Included in the term alkyl is the alkyl portion of higher acyl radicals). Examples of this group of synthetic detergents which form a part of the preferred compositions of the present invention are the alkali metal, e.g. sodium or potassium, alkyl sulfates, especially those obtained by sulfating the higher alcohols (8 to 18 carbon atoms) produced by reducing the glycerides of tallow or coconut oil; the alkali metal olefin sulfonates of from 8 to 24 carbon atoms described, for example, in U.S. Pat. No. 3,332,880; and the alkali metal alkyl glyceryl ether sulfonates, especially those ethers of the higher alcohols derived from tallow and coconut oil. Other anionic detergents include the alkali metal alkylbenzene sulfonates, in which the alkyl group contains from 9 to 15 carbon atoms, including those of the types described in U.S. Pat. Nos. 2,220,099 and 2,477,383 (the alkyl radical can be a straight or branched aliphatic chain); sodium coconut oil fatty acid monoglyceride sulfates and sulfonates; salts of alkyl phenol ethylene oxide ether sulfates with 1 to 12 units of ethylene oxide per molecule and in which the alkyl radicals contain from 8 to 18 carbon atoms; the reaction product of fatty acids esterified with isethionic acid and neutralized with sodium hydroxide where, for example, the fatty acid is oleic or derived from coconut oil; sodium or potassium salts of fatty acid amides of a methyl tauride in which the fatty acids, for example, are derived from coconut oil; sodium or potassium $\beta$-acetoxy- or $\beta$-acetamido-alkanesulfonates where the alkane has from 8 to 22 carbon atoms; and others known in the art. A number are specifically set forth in U.S. Pat. Nos. 2,286,921; 2,486,922; and 2,396,278.

A further class of surfactants falling within this category are water-soluble salts of the organic, sulfuric acid reaction products of straight or branched, saturated, aliphatic hydrocarbon radicals having from 8 to 24, preferably from 12 to 18 carbon atoms, particularly hydrocarbon radicals of the methane series, including iso-, neo-, meso-, and n-paraffins. Water-soluble salts of $C_{14}$-$C_{16}$ sulfonated paraffins are especially preferred.

Other synthetic anionic detergents useful herein are alkyl ether sulfates. These materials have the formula $R^2O(C_2H_4O)_xSO_3$ wherein $R^2$ is alkyl or alkenyl of about 8 to 24 carbon atoms, $x$ is 1 to 30, and M is a salt-forming cation selected from alkali metal, ammonium and dimethyl-, trimethyl-, triethyl-, dimethanol-, diethanol-, trimethanol- and triethanol- ammonium cations.

The alkyl ether sulfates are condensation products of ethylene oxide and monohydric alcohols having about 8 to 24 carbon atoms. Preferably, $R^2$ has 14 to 18 carbon atoms. The alcohols can be derived from fats, e.g. coconut oil or tallow, or can be synthetic. Lauryl alcohol and straight-chain alcohols derived from tallow are preferred herein. Such alcohols are reacted with from 1 to 12, especially 6, molar proportions of ethylene oxide and the resulting mixture of molecular species, having, for example an average of 6 moles of ethylene oxide per mole of alcohol, is sulfated and neutralized.

The alkyl ether sulfates are described in U.S. Pat. No. 3,332,876.

B. Nonionic Synthetic Detergents

Nonionic synthetic detergents may be broadly defined as compounds produced by the condensation of alkylene oxide groups (hydrophilic in nature) with an organic hydrophobic compound, which may be aliphatic or alkyl aromatic in nature.

One class of nonionic synthetic detergents is commercially available under the Trade Name of 'Pluronic'. These compounds are formed by condensing ethylene oxide with a hydrophobic base having a molecular weight in the range 1500–1800 and formed by the condensation of propylene oxide with propylene glycol.

Other suitable nonionic synthetic detergents include the following:

1. The polyethylene oxide condensates of alkyl phenol, e.g. the condensation products of alkyl phenols having an alkyl group containing from 6 to 12 carbon atoms, in either a straight-chain or branched-chain configuration, with ethylene oxide, the ethylene oxide being present in amounts equal to 5 to 25 moles of ethylene oxide per mole of alkyl phenol. The alkyl substituent in such compounds may be derived, for example, from polymerised propylene, diisobutylene, octene or nonene. Specific examples include nonyl phenol condensed with 20 moles of ethylene oxide, dodecyl phenol condensed with 15 moles of ethylene oxide and diisooctyl phenol condensed with 15 moles of ethylene oxide.

2. Those derived from the condensation of ethylene oxide with a hydrophobic base formed by the product resulting from the reaction of propylene oxide and ethylene diamine. Bases having a molecular weight of the order of 2,500 to 3,000 are satisfactory and typical compounds contain from 40 to 80% polyoxyethylene by weight and have a molecular weight of from 5,000 to 11,000.

3. The condensation product of aliphatic alcohols having from 8 to 24 carbon atoms, in either straight-chain or branched-chain configuration with ethylene oxide, e.g. a coconut alcohol-ethylene oxide condensate having from 5 to 30 moles of ethylene oxide per mole of coconut alcohol, the coconut alcohol fraction having from 10 to 14 carbon atoms.

4. Other particularly preferred materials are synthetic primary alcohol ethoxylates available from the Shell Oil Company under the trade marks 'Dobanol' and 'Neodol', from Imperial Chemical Industries Ltd. under the trade mark 'Synperonic', and from Liquichimica SA under the trade name 'Lial'.

Specific examples of these synthetic alcohol ethoxylates include Dobanol 45E7, a $C_{14}$–$C_{15}$ predominantly linear alcohol containing up to 25% 2-methyl branching condensed with an average of seven moles of ethylene oxide, Dobanol 91E8, a $C_9$–$C_{11}$ predominantly linear alcohol condensed with an average of eight moles of ethylene oxide, and Synperonic E-3, a condensation product of 3 moles of ethylene oxide with one mole of an alcohol mixture comprising a 2:1 ratio of $C_{13}$–$C_{15}$ primary alcohols with 50% 2-methyl branching.

5. A detergent having the formula $R^3R^4R^5N\rightarrow O$ (amine oxide detergent) wherein $R^3$ is an alkyl group containing from 10 to 28 carbon atoms, from 0 to 2 hydroxy groups and from 0 to 5 ether linkages, there being at least one moiety of $R^3$ which is an alkyl group containing from 10 to 18 carbon atoms and 0 ether linkages, and $R^4$ and $R^5$ are each selected from alkyl radicals and hydroxyalkyl radicals containing from 1 to 3 carbon atoms.

Specific examples of amine oxide detergents include: dimethyldodecylamine oxide, dimethyltetradecylamine oxide, ethylmethyltetradecylamine oxide, cetyldimethylamine oxide, dimethylstearylamine oxide, cetylethylpropylamine oxide, diethyldodecylamine oxide, diethyltetradecylamine oxide, dipropyldodecylamine oxide, bis-(2-hydroxyethyl) dodecylamine oxide, bis-(2-hydroxyethyl)-3-dodecoxy-1-hydroxypropylamine oxide, (2-hydroxypropyl)methyltetradecylamine oxide, dimethyloleylamine oxide, dimethyl-(2-hydroxydodecyl) amine oxide, and the corresponding decyl, hexadecyl and octadecyl homologues of the above compounds.

6. A detergent having the formula

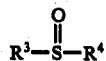

wherein $R^3$ and $R^4$ are as defined above. Specific examples of sulfoxide detergents include dodecyl methyl sulfoxide, tetradecyl methyl sulfoxide, 3-hydroxytridecyl methyl sulfoxide, 3-methoxytridecyl methyl sulfoxide, 3-hydroxy-4-dodecoxybutyl methyl sulfoxide, octadecyl 2-hydroxyethyl sulfoxide and dodecylethyl sulfoxide.

7. The ammonia, monoethanol and diethanol amides of fatty acids having an acyl moiety of from 8 to 18 carbon atoms. These acyl moieties are normally derived from naturally occurring glycerides, e.g. coconut oil, palm oil, soybean oil and tallow but can be derived synthetically, e.g. by the oxidation of petroleum, or by hydrogenation of carbon monoxide by the Fischer Tropsch process.

C. Ampholytic Synthetic Detergents

Ampholytic synthetic detergents can be broadly described as derivatives of aliphatic or aliphatic derivatives of heterocyclic secondary and tertiary amines, in which the aliphatic radical may be straight-chain or branched and wherein one of the aliphatic substituents contain from 8 to 18 carbon atoms and at least one contains an anionic water-solubilizing group, e.g. carboxy, sulfo or sulfato. Examples of compounds falling within this definition are sodium 3-(dodecylamino)propionate, sodium 3-(dodecylamino)propane-1-sulfonate, sodium 2-(dodecyl-amino)-ethylsulfate, sodium 2-(dimethylamino)-octadecanoate, disodium octadecyliminodiazetate, sodium 1-carboxymethyl-2-undecyl imidazole, and sodium N,N-bis-(2-hydroxyethyl)-2-sulfato 3-dodecoxypropylamine.

D. Zwitterionic Synthetic Detergents

Zwitterionic synthetic detergents can be broadly described as derivatives of aliphatic quaternary ammonium and phosphonium or tertiary sulfonium compounds, in which the cationic atom may be part of a heterocyclic ring, and in which the aliphatic radical may be straight-chain or branched and wherein one of the aliphatic substituents contains from 3 to 18 carbon atoms, and at least one aliphatic substituent contains an anionic water-solubilizing group, e.g. carboxy, sulfo or sulfato. Examples of compounds falling within this definition are 3-(N,N-dimethyl-N-hexadecyl-ammonio)-2-hydroxypropane-1-sulfonate, 3-(N,N-dimethyl-N-hexadecylammonio)-propane-1-sulfonate, 2-(N,N-dimethyl-N-dodecylammonio)acetate, 3-(n,N-dimethyl-N-dodecylammonio) propionate, 2-(N,N-dimethyl-N-octadecylammonio)-ethyl sulfate, 2-(S-methyl-S-tert-hexadecyl-sulfonio)ethane-1-sulfonate, 3-(S-methyl-S-dodecyl-sulfonio) propionate, 4-(S-methyl-S-tetradecyl-sulfonio) butyrate, 1-(2-hydroxy-ethyl)2-undecyl imidazolium-1-acetate, 2-(trimethylammonio) octadecanoate, and 3-(N,N-bis-(2-hydroxyethyl)-N-octadecylammonio)-2-hydroxy propane-1-sulfonate and 3-(N,N-dimethyl-N-1-methyl alkyl ammonio)-2-hydroxy propane-1-sulfonate, wherein alkyl averages 13.5 to 14.5 carbon atoms in length. Some of these detergents are described in U.S. Pat. Nos. 2,129,264; 2,178,353; 2,774,786; 2,813,898 and 2,828,332.

The soap and non-soap anionic, nonionic and zwitterionic detergent surfactants mentioned above can be used as the sole surface-active agents, or the various examples may be mixed when used in the practice of the invention. Especially preferred are anionic and nonionic surface-active agents. The amount of surface-active agent incorporated in the preparation depends upon the intended use of the particular formulation. Thus it will relate to the weight of the preparation as a whole, when it is applied directly to skin or hair, e.g. as a shampoo, or the concentration at which it will be used as a solution in, for example, dishwashing water or bath water. In most cases a content within the range of 0.1 to 90% by weight of the preparation is suitable. More particularly, detergent compositions for cleaning purposes will generally comprise between 5 and 50% by weight of surface-active agent, preferably between 10 and 30% of surface active agent.

The invention is applicable to a variety of detergent compositions which may come into contact with keratin in the normal course of use, for example dishwashing liquids, hair shampoos, bathing compositions, heavy-duty detergent compositions, hard-surface-cleaning compositions and bar soaps. The physical form of the composition may vary widely, from granular solids, through gels and creams, to viscous or mobile liquid compositions. Dishwashing compositions are generally liquid and comprise mixtures of water and foaming detergents. Granular detergent compositions on the other hand, may contain little or no free water.

The preferred liquid or granular detergent compositions for use, for instance, as heavy-duty detergents, dishwashing compositions or shampoos, comprise between 5 and 50% by weight of foaming detergent.

More especially, the foaming detergent is selected from:

a. From 0 to 45% of a water-soluble hydrocarbon sulfate of the general formula $R^2O(C_2H_4O)_nSO_3M$ wherein $R^2$ is a straight or branched, saturated or unsaturated aliphatic, hydrocarbon radical having from 8 to 24 carbon atoms, n is from 1 to 12; and M is an alkali or alkali earth metal, ammonium or dimethyl-, trimethyl-, triethyl-, dimethanol-, diethanol-, trimethanol- or triethanol- ammonium cation;

b. From 0 to 45% by weight of a water-soluble hydrocarbon sulfonate of the general formula $R^3SO_3M$; wherein $R_3$ is a straight or branched chain saturated or unsaturated $C_8$-$C_{24}$ aliphatic hydrocarbon radical or a $C_8$-$C_{18}$ straight or branched chain alkyl benzene radical and M is as defined above;

c. From 0 to 45% by weight of a water-soluble hydrocarbon sulfate of the general formula $R^2OSO_3M$; where M and $R_2$ are as defined above;

d. From 0 to 10% by weight of an ammonia, monoethanol or diethanol amide of a fatty acid having an acyl moiety of from 8 to 18 carbon atoms;

e. Up to 40% by weight of the condensation product of from 3 to 25 moles of an alkylene oxide, preferably ethylene or propylene oxide, and one mole of an organic, hydrophobic compound, aliphatic or alkyl aromatic in nature, the latter having from 8 to 24 carbon atoms; and f. From 0 to 10% of a trialkyl amine oxide of formula

wherein $R_4$ is an alkyl group containing from 10 to 28 carbon atoms and $R_5$ and $R_6$ are each selected from alkyl radicals and hydroxyalkyl radicals containing from 1 to 3 carbon atoms.

Granular detergents conventionally contain from 5 to about 20% by weight of the composition of foaming surfactant normally a $C_{10}$-$C_{14}$ linear alkyl benzene sulfonate, alone or in admixture with a higher alkyl sulfate such as a synthetic or naturally derived $C_{16}$-$C_{18}$ alkyl sulphate, e.g. tallow alkyl sulfate. Optional ingredients of such mixtures are also higher alkyl ethoxysulfates such as those disclosed in German Laid Open Applications DOS Nos. 2355940 and 2355983, both incorporated herein by reference.

Nonionic surfactants such as ethoxylated primary or secondary alcohols and/or alkyl amides and ethanolamides may also be present at levels up to 10% of the composition.

Dishwashing liquid products in accordance with the invention can contain up to 45% surfactant by weight of the composition. Typical formulations include 15-30% of a linear alkylbenzene sulfonate and 15-30% of a $C_{10}$-$C_{18}$ linear alkyl ethoxy sulfate containing an average of 1-6 ethoxy groups. Another preferred formulation includes 5-15% of a $C_{14}$-$C_{16}$ paraffin sulfonate, 5-15% of $C_{12}$ alkyl triethoxysulfate and 1-10% of each of $C_{12}$ amine oxide, coconut alcohol hexaethoxylate and lauric diethanolamide. Another dishwashing liquid having mild properties to skin includes from about 15 to about 25% of a $C_{12}$-$C_{14}$ alkyl ether sulfate containing an average of from about 3 to about 12 ethylene oxide groups, up to about 10% of a $C_{12}$-$C_{14}$ alkyl sulfate, from about 1% to about 5% of a $C_{12}$-$C_{14}$ alkyl glyceryl ether sulfonate and from about 2% to about 6% of a $C_{12}$-$C_{14}$ alkyl dilower alkyl amine oxide.

A further preferred liquid detergent composition contains from 10-25% by weight of a water-soluble saturated hydrocarbon sulfonate, from 1-10% by weight of an alkyl ether sulfate and from 1-15% by weight of a water-soluble solvent such as a lower alkanol, in addition to the usual minor ingredients such as perfume, colour, buffers, anti-tarnish agents etc.

The liquid detergent or gel compositions of the invention generally comprise a carrier based upon water and/or a water-soluble solvent. Suitable solvents include $C_{2-8}$ mono and di-alcohols, e.g. ethanol, butanol, methyl propanol-1 and -2, amylol or pentanol, butanediol, toluol, benzyl carbinol, ethyleneglycol monobutyl ether, propyleneglycol propyl ether and diethyleneglycol dimethyl ether. They are generally present in amounts up to 15% by weight of the composition. Additional components of liquid detergent compositions include buffer materials, foam boosters, such as higher alkyl ($C_{12}$-$C_{14}$) amine oxides and alkylolamides of $C_{10}$-$C_{14}$ carboxylic acids, thickeners, preservatives, opacifiers, perfumes, dyes, fluorescers, tarnish inhibitors, bactericides, hydrophobic oily materials and hydrotropes. Commonly employed hydrotropes include conventional lower alkylaryl sulfonates such as sodium and potassium toluene sulfonate, xylene sulfonate, benzene sulfonate and cumene sulfonate at levels of up to 10% normally in the range 2-6% by weight of the composition. Urea and lower alkanol hydrotropes such as methanol, ethanol, propanol and butanol may also be used at levels of 1-15%, normally 5-15% by weight of the composition.

Hydrophobic oily materials suitable for use in the present invention include animal, vegetable and mineral oils and waxes, for example beeswax, spermaceti and carnauba wax; fatty alcohols such as stearyl, myristyl and cetyl alcohols; fatty esters and partial esters such as isopropyl myristate and glyceryl monostearate; fatty acids such as stearic acid; lanolin and cholesterol derivatives; and silicone oils. The compositions of the invention may also comprise components designed to enhance the moisturizing effectiveness of the compositions. Suitable components include lower aliphatic alcohols having from 2 to 6 carbon atoms and 2 to 3 hydroxy groups, for example 1,4 butanediol, 1,2-propylene glycol and glycerine. Other suitable components include urea or urea derivatives such as guanidine, pyrrolidone or allantoin.

Soild granular detergent compositions may contain foam enhancers, foam depressants, bleaches, antiredeposition agents, enzymes, enzyme and bleach activators, fluorescers, builders and other normal components of granular detergent compositions. Solid compositions in bar form may also contain additives such as fatty acids, salts, skin creams and oils.

Skin Conditioning Tests

Conditioning performance was measured in both in-vitro and in-vivo tests, a high degree of correlation between the two test methods being found. The in-vitro test (called the calf-skin occlusivity test) was based upon the rate of water transpiration through a sample of calf-skin brought into contact with a 0.15% aqueous solution of a detergent composition (at 18° hardness) containing the protein. The occlusivity of the protein was measured as the percentage reduction in the rate of water transpiration for the proteinaceous surfactant solution compared with that for water.

One in-vivo test used was hand-immersion testing (HIT). This test used a group of normal housewives in a multi-product test; hands were balanced for right hand/left hand differences, so that there were 32 hands per product, 16 right and 16 left. Each person immersed left and right hands in different solutions for three consecutive 10 minute periods in half an hour per day, for 2 weeks, 5 days per week. Treatment solutions were replenished every 10 minutes. Hands were withdrawn and reimmersed in the solution every 2 minutes. Hands were graded on the starting Monday (before immersion) and on each Friday of the test.

HIT grades for protein/surfactant solutions were determined and are quoted here, on a scale in which an 0.15% aqueous solution of a standard detergent was assigned HIT grades of 0, and a 1mg/cm$^2$ application of hand-care lotion was assigned HIT grades of 100.

A second in-vivo test was also used which compares the rate of water loss through skin, specifically human forearm skin, under controlled conditions before and after treatment with a test solution. The lower the rate of water loss, the greater the ability of the skin to bind moisture and hence the greater the resistance to chapping, cracking etc.

A test area of skin was treated with a compound (Poldine methyl sulfate) that inhibits sweating and the treated areas was then swept with dry nitrogen and the water content of the gas assayed before and after passage over the skin. The Test area was immersed in an 0.15% product solution for 10 minutes at 45° C (Water hardness = 18° H), dried and allowed to equilibrate for 1 hour before a further reading was obtained of the water content of a dry nitrogen stream passed over the treated skin surface. The change in water loss before and after treatment expressed as a percentage of the water loss before treatment gives the relative skin conditioning power of the particular protein.

Non-limitative embodiments of the invention are set out in the following examples.

EXAMPLE I

A liquid detergent composition, having the formulation shown below, was prepared and compared for conditioning effectiveness against a standard liquid dishwashing composition containing no protein.

| Composition | Example I | Standard |
|---|---|---|
| Ammonium linear $C_{12}$–$C_{14}$ alkyl benzene sulfonate | 18.4 | 18.4 |
| Sodium linear $C_{12}$–$C_{14}$ alcohol sulfate including 3 ethylene oxide moieties | 18.4 | 18.4 |
| Lauric monoethanolamide | 2.0 | 4.5 |
| Industrial methylated spirits | 11.0 | 11.0 |
| Protein | 4.0 | — |
| Magnesium chloride | 2.1 | — |
| Water | To 100 | To 100 |
| Performance | | |
| In Vitro Occlusivity | 9.4 | −6.1 |
| Hand Immersion Testing | 43 | 0 |

The protein used in the above example was obtained from soyprotein isolate by hydrolysis with sodium hydroxide followed by hydroxyalkylation with butylene oxide, as described earlier. The protein had a molecular weight of about 3000, and isoionic point pH of 5.9 and a degree of hydroxyalkylation of about 50% of free carboxylic acid groups. The protein is thus seen to be particularly effective in protecting skin from the deleterious effects of detergent, both in-vivo and in-vitro.

EXAMPLE II

Two liquid detergent compositions identified as A & B were made up and tested using the in-vivo test method set out previously for assessing the water loss through skin.

Composition A was in accordance with the Standard in Example I and contained no modified protein.

Composition B had the following ingredients:

| | B |
|---|---|
| Ammonium $C_{12}$–$C_{14}$ linear alkyl benzene sulfonate | 18.4 |
| Sodium $C_{12}$–$C_{14}$ linear triethoxy alkyl sulfate | 18.4 |
| $C_{12}$ monoethanolamide | 2.0 |
| Industrial Methylated Spirits | 13.0 |
| Single Cell Protein* acetylated alkaline hydrolyzate in which acetylation of the amino groups was substantially complete. Estimated pI = 3 − 4 | 3.6 |
| Water | To 100 |

*Toprina G, a protein derived from yeast cultured on purified alkines and supplied by British Petroleum Ltd.

In the above-mentioned in-vivo test the two compositions performed as follows:

| A | + 20 ± 10.5% | i.e. an increase in water loss as a result of the treatment |
|---|---|---|
| B | −27 ± 11% | |

It can be seen that composition B (acetylated, hydrolyzed single cell protein) is significantly better than composition A which is a proteinfree standard.

EXAMPLE III

Three liquid detergent compositions identified as C–E were made up and tested using the in-vivo test method employed in Example II. Each composition had the Base formulation of composition B of Example II and contained 3% by weight protein as follows:

| Composition | |
|---|---|
| C | Alkali-hydrolyzed Whey protein (pI = 5.0) |
| D | Alkali-hydrolyzed acetylated Whey protein; estimated pI = 3 − 4, in which substantially all of the amino groups were acetylated. |
| E | Alkali-hydrolyzed acetylated soybean protein in which substantially all the amino groups were acetylated. |

In the in-vivo test, the composition had the following performance:

| C | + 3 ± 8% |
|---|---|
| D | − 7.5 ± 8% |
| E | − 15.5 ± 5% |

It can be seen that compositions D and E containing proteins modified in accordance with the invention provide an occlusive benefit.

EXAMPLE IV

The composition of Example IV was the same as Example I except that the protein was prepared by hydrolysis of soyprotein isolate followed by acylation with acetic anhydride, as described above. The N-acetylated protein had an isoionic point pH of 3, a molecular weight of about 3000 and a degree of N-acylation of about 100% of -amino acids. The hand immersion test value for Example IV was 48.

EXAMPLES V to X

The following examples serve to illustrate, but not to limit, liquid detergent compositions according to the present invention. All percentages indicated are by weight:

| | EXAMPLES | | | | | |
|---|---|---|---|---|---|---|
| | V | VI | VII | VIII | IX | X |
| Dimethyldodecyl amine oxide | 8% | 4% | 2% | 4% | 2% | 4% |
| Coconut alcohol ethylene oxide (6) condensate | 15 | 7 | 6 | 7 | 2 | 7 |
| Diethanol $C_{12-16}$ fatty acid amide | 2 | — | 3 | — | 2 | — |
| Coconut alcohol ethylene oxide (3) sulfate sodium salt | — | 10 | 9 | 14 | 10 | 12 |
| $C_{13-18}$ paraffin sulfonate sodium salt | — | 10 | 9 | — | 9 | 10 |
| $C_{12-14}$ alpha-olefin sulfonate, ammonium salt | — | — | — | 12 | — | — |
| Urea | 8 | 6 | — | 10 | 8 | 6 |
| Industrial Methylated Spirits | 11 | 13 | 13 | 13 | 13 | 12 |
| *Modified Soyprotein | 2 | 4 | 4 | 4 | 5 | 3 |
| Water | | | | Balance | | |

*Modified soyprotein: hydroxybutyl derivative of NaOH hydrolyzed Promine F; molecular weight 3000; isoionic point 5.9; percentage of 0-alkylated side chains 50.

The above compositions are milder to skin and hair than the corresponding compositions containing no modified protein and there is substantially no diminution in the volume or the stability of foam produced by the detergent. Substantially similar cleaning and conditioning performance is obtained when the modified protein in the above example is replaced by N-acetyl whole casein, N-butyryl whey protein, N-hexanoyl gelatin, N-acetyl soyprotein, hydroxypropylated cottonseed protein and the corresponding modified derived proteins in which the derived protein has been obtained by acidic or basic hydrolysis or by reduction with, for example, sodium borohydride.

EXAMPLE XI

A dishwashing liquid which is mild to skin has the following composition:

| | Parts by wt. |
|---|---|
| Coconut alcohol-ethylene oxide (12) sulfate ammonium salt | 18.75 |
| Coconut alcohol sulfate, ammonium salt | 5.8 |
| Sodium alkyl glyceryl ether sulfonate (where the alkyl is derived from "middle-cut" coconut alcohols and has the following approximate composition: 2% $C_{10}$; 66% $C_{12}$; 23% $C_{14}$; 9% $C_{16}$ | 4.0 |
| Coconut alkyl dimethyl amine oxide (wherein the coconut is middle cut) | 5.0 |
| Potassium toluene sulfate | 0.5 |
| Potassium chloride | 2.5 |
| Citric acid | 0.1 |
| Hydrogen chloride | 0.81 |
| Ammonium Xylene sulfate | 5.0 |
| Ethanol | 8.75 |
| Protein - N-acetylated alkali degraded Promine F; isoionic point 3.0; molecular weight 3000 | 4.0 |
| Water | To 100 |

Similar results are obtained when the protein is replaced by N-acetylated whole casein.

EXAMPLE XII

A soap bar composition which is mild to skin has the following composition:

| | Parts by wt. |
|---|---|
| Real soap (Tallow/coconut = 50/50) | 78.5 |
| Free fatty acid | 7.6 |
| Moisture | 9.3 |
| Skin cream | 0.5 |
| Hydroxybutylated alkali degraded Promine F; isoionic point 5.9; Molecular weight 3000 | 4.0 |

EXAMPLES XIII-XVI

Granular detergent compositions were prepared with the following compositions:

| | Example XIII | Example XIV | Example XV | Example XVI |
|---|---|---|---|---|
| Sodium linear dodecyl sulfonate | — | 6 | 6 | — |
| Sodium tallow alkyl sulfate | — | 4 | 4 | — |
| Sodium soap (90 Tallow/10 Coconut | 0.5 | 2.5 | 2.5 | 0.5 |
| Coconut monoethanolamide | — | 1.5 | 1.5 | — |
| Tallow monoethanolamide | 0.25 | — | — | 0.25 |
| 3-(N,N-dimethyl-N-$C_{14.8}$-alkylammonio)-2-hydroxypropane-1-sulfonate) | 6 | — | — | 6 |
| Tergitol 15-S-9 | 6 | — | — | 6 |
| Sodium tripolyphosphate | 2 | 33 | 10 | 2 |
| Sodium silicate | 37.5 | 7 | 7 | 7 |
| Sodium carboxymethyl cellulose | 0.5 | 0.5 | 0.5 | 0.5 |
| Sodium sulfate | 34 | 8 | 31 | 30 |
| Sodium perborate | 25 | 25 | 8 | 25 |
| Sodium chloride | 1.5 | — | — | 1.5 |
| Protease | Present | Present | Present | Present |
| Sodium EDTA | 0.25 | 0.25 | 0.25 | 0.25 |
| Perfume/brighteners | 0.6 | 0.6 | 0.6 | 0.6 |
| Inert impurities | 3.9 | 0.65 | 0.65 | 3.9 |
| Moisture | 7 | 7 | 7 | 7 |
| Protein | 4 | 4 | 4 | 4 |

The protein was an N-acetylated alkali degraded soyprotein having an isoionic point of 3 and a molecular weight of about 3000.

EXAMPLE XVII

The following liquid detergent composition was made up:

|  | Wt% |
|---|---|
| Sodium C$_{14}$ alkane sulfonate | 14.4 |
| Sodium coconut alkyl triethoxy sulfate | 3.6 |
| Ethyl Alcohol | 5.0 |
| Colour Perfume etc. | 0.1 |
| Water | To 100 |

Acetylated hydrolyzed soyprotein of pI 3.0 was then added to a sample of the formulation at a level of 4% of the composition and both formulations were tested in-vivo for the rate of water loss through forearm skin using the test described herein.

Results were as follows:

| Base formulation | + 3 ± 7% |
|---|---|
| Base formulation with acetylated soyprotein | − 9 ± 7% |

The composition in accordance with the invention can be seen to provide a reduction in water loss from the skin whilst the base composition does not give the same benefit.

What is claimed is:

1. A composition for protecting keratinous material from the deleterious effects of detergents or from adverse climatic conditions, said composition comprising
   (a) from 0.1 to 90% by weight of a foaming non cationic detergent material; and
   (b) from 0.1 to 20% by weight of a chemically modified protein having an isoionic point (pI) less than pH of 6, said chemically modified protein being selected from the group consisting of oxybutylated hydrolyzed protein and acetylated hydrolyzed protein.

2. A composition as recited in claim 1, in which the chemically modified protein is present in an amount between 2 and 6% by weight.

3. A composition as recited in claim 2, in which the chemically modified protein has a molecular weight in the range from 2000 to 5000.

4. A composition as recited in claim 3, in which the chemically modified protein is oxybutylated base hydrolyzed soy protein isolate.

5. A composition as recited in claim 3, in which the chemically modified protein is acetylated base hydrolyzed soy protein isolate.

6. A composition as recited in claim 3, in which the chemically modified protein is acetylated base hydrolyzed whey.

7. A composition recited in claim 3, in which the chemically modified protein is acetylated base hydrolyzed protein derived from yeast.

8. A composition as recited in claim 3, in which the chemically modified protein has a pI in the range of from pH2.5 to pH5.5.

UNITED STATES PATENT OFFICE
CERTIFICATE OF CORRECTION

PATENT NO. : 4,076,800
DATED : February 28, 1978
INVENTOR(S) : ROBERT ANTHONY MARSH ET AL It is certified that error appears in the above-identified patent and that said Letters Patent are hereby corrected as shown below:

Delete the terminal disclaimer notice.

Signed and Sealed this

Third Day of April 1979

[SEAL]

Attest:

RUTH C. MASON
Attesting Officer

DONALD W. BANNER
Commissioner of Patents and Trademarks